(12) United States Patent
Perez

(10) Patent No.: US 11,033,395 B2
(45) Date of Patent: Jun. 15, 2021

(54) CONSTRAINED SHELL FOR MODULAR DUAL MOBILITY SYSTEM

(71) Applicant: Howmedica Osteonics Corp., Mahwah, NJ (US)

(72) Inventor: Alvin Perez, Ringwood, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 194 days.

(21) Appl. No.: 15/886,235

(22) Filed: Feb. 1, 2018

(65) Prior Publication Data

US 2018/0214274 A1 Aug. 2, 2018

Related U.S. Application Data

(60) Provisional application No. 62/453,733, filed on Feb. 2, 2017.

(51) Int. Cl.
*A61F 2/32* (2006.01)
*A61F 2/34* (2006.01)
*A61F 2/30* (2006.01)

(52) U.S. Cl.
CPC ............ *A61F 2/34* (2013.01); *A61F 2/30724* (2013.01); *A61F 2/32* (2013.01);
(Continued)

(58) Field of Classification Search
CPC ................ A61F 2/34; A61F 2002/3208; A61F 2002/3611; A61F 2/32; A61F 2/36;
(Continued)

(56) References Cited

U.S. PATENT DOCUMENTS

| 4,279,041 A | 7/1981 | Buchholz |
| 4,437,193 A | 3/1984 | Oh |

(Continued)

FOREIGN PATENT DOCUMENTS

| DE | 93121510 U1 | 10/1993 |
| EP | 1179324 A2 | 2/2002 |

(Continued)

OTHER PUBLICATIONS

Extended European Search Report for EP Application No. 18154625. 0, dated Oct. 23, 2018, pp. 1-6.

(Continued)

*Primary Examiner* — Ann Schillinger
(74) *Attorney, Agent, or Firm* — Lerner, David, Littenberg, Krumholz & Mentlik, LLP

(57) ABSTRACT

An insert is advanced and at least partially secured into a prosthetic device configured for use in a joint. The prosthetic device includes a shell with a cavity defined by an interior surface. The interior surface includes first and second portions that share an edge and that abut an edge of the interior surface. The first portion includes a partially spherical surface while the second portion is a partially cylindrical shape. A maximum radius of the second portion is larger than a radius of the first portion. A center defining the maximum radius of the second portion is offset from a center defining the radius of the first portion. The geometry of the interior surface allows the insert to be advanced into the shell in a single orientation. When advanced sufficiently into the shell, the insert is rotated to constrain the insert within the shell.

20 Claims, 8 Drawing Sheets

(52) U.S. Cl.
CPC ............... *A61F 2002/3208* (2013.01); *A61F 2002/3233* (2013.01); *A61F 2002/3443* (2013.01)

(58) Field of Classification Search
CPC .......... A61F 2/4609; A61F 2002/30324; A61F 2002/30332; A61F 2/3609; A61F 2002/3446; A61F 2230/0076; A61F 2250/0036; A61F 2/605
See application file for complete search history.

(56) References Cited

U.S. PATENT DOCUMENTS

| | | | |
|---|---|---|---|
| 5,370,703 | A | 12/1994 | Willert et al. |
| 5,383,938 | A | 1/1995 | Rohr et al. |
| 5,725,587 | A | 3/1998 | Garber |
| 5,879,399 | A | 3/1999 | Church |
| 5,916,270 | A | 6/1999 | Lipman |
| 5,964,809 | A | 10/1999 | Lin et al. |
| 6,520,995 | B2 | 2/2003 | Church |
| 6,626,947 | B2 | 9/2003 | Lester et al. |
| 7,074,241 | B2 | 7/2006 | McKinnon |
| 7,335,231 | B2 | 2/2008 | McLean |
| 7,393,362 | B2 | 7/2008 | Cruchet et al. |
| 7,455,694 | B2 | 11/2008 | Epaules et al. |
| 7,520,902 | B2 | 4/2009 | Deloge et al. |
| 7,682,398 | B2 | 3/2010 | Croxton et al. |
| 7,708,783 | B2 | 5/2010 | Richards |
| 7,749,277 | B2 | 7/2010 | McLean |
| 7,780,739 | B2 | 8/2010 | Lakin et al. |
| 8,029,571 | B2 | 10/2011 | McLean |
| 8,029,572 | B2 | 10/2011 | McLean |
| 8,398,718 | B2 | 3/2013 | Richardson et al. |
| 8,465,549 | B2 | 6/2013 | Richardson |
| 9,023,112 | B2 | 5/2015 | Komistek |
| 9,060,862 | B2 | 6/2015 | Castro et al. |
| 2002/0040245 | A1 | 4/2002 | Lester et al. |
| 2002/0049500 | A1 | 4/2002 | Draenert |
| 2002/0116068 | A1* | 8/2002 | McLean ............... A61F 2/3609 623/22.15 |
| 2003/0017817 | A1 | 1/2003 | Cowley |
| 2003/0171817 | A1 | 9/2003 | Rambert et al. |
| 2006/0241780 | A1 | 10/2006 | McKinnon |
| 2012/0109327 | A1 | 5/2012 | Forsell |
| 2012/0197412 | A1 | 8/2012 | Gradel |
| 2012/0209397 | A1 | 8/2012 | Richardson |
| 2012/0209398 | A1 | 8/2012 | Richardson et al. |
| 2015/0250596 | A1 | 9/2015 | Whitaker et al. |
| 2015/0335437 | A1 | 11/2015 | Bruun Lauritzen et al. |
| 2016/0250027 | A1 | 9/2016 | Bal et al. |

FOREIGN PATENT DOCUMENTS

| | | | | |
|---|---|---|---|---|
| EP | 1520559 | A1 | 4/2005 | |
| EP | 1582182 | A1 | 10/2005 | |
| EP | 1776934 | A1 * | 4/2007 | ............... A61F 2/32 |
| EP | 1776934 | A1 | 4/2007 | |
| EP | 2489333 | A1 | 8/2012 | |
| FR | 2430221 | A1 | 2/1980 | |
| FR | 2516377 | A1 | 5/1983 | |
| FR | 2770769 | A1 | 5/1999 | |
| FR | 2771922 | A1 | 6/1999 | |
| FR | 2785525 | A1 | 5/2000 | |
| FR | 2795302 | A1 | 12/2000 | |
| FR | 2807315 | A1 | 10/2001 | |
| FR | 2929103 | A1 | 10/2009 | |
| FR | 2951071 | A1 | 4/2011 | |
| WO | 0176511 | A1 | 10/2001 | |
| WO | 02058597 | A2 | 8/2002 | |
| WO | 2007056678 | A2 | 5/2007 | |
| WO | 2009118673 | A1 | 10/2009 | |
| WO | 2014094785 | A2 | 6/2014 | |

OTHER PUBLICATIONS

Constrained Acetabular Insert, Surgical Protocol, Stryker, 2011, USA.
MDM X3: Modular Dual Mobility Acetabular System, Surgical Technique, Stryker, 2012, USA.
Trident Constrained Acetabular Insert: Surgical Protocol, Stryker, 2012, USA.
Trident Constrained Acetabular Inserts: Stability Matters, Stryker, 2006, USA.
Trident Revision Options, Stryker Howmedica Osteonics, 2001, USA.

* cited by examiner

CONSTRAINED SHELL FOR MODULAR DUAL MOBILITY SYSTEM

This application claims the benefit of the filing date of U.S. Provisional Patent Application No. 62/453,733, filed Feb. 2, 2017, the disclosure of which is hereby incorporated by reference herein.

BACKGROUND OF THE INVENTION

Prosthetic devices have been used to supplement or replace components of ball-and-socket joints of the body. Such devices have included liners dimensioned to accommodate placement and securement of an insert into the liner. One example of such securement involves a "snap fit" where the insert snaps into place within the liner. Such devices are often limited in the mobility offered. Other examples include liners with irregularly shaped interior surfaces within a cavity of the liner to aid in constraint of inserts when disposed therein. For these devices, an ability to constrain an insert may be limited. Other devices require an insert to be translated after advancement but prior to rotating the insert into a constrained position. Without translation in such devices, interior walls of a corresponding liner prevent rotation. This translation requirement increases cycle time during fabrication. Still further devices incorporate locking mechanisms or other elements to aid in constraint of an insert into a liner. Such devices are thus more prone to failure due to the additional components necessary to achieve the constraint function.

Thus, there is a need for improvement in devices, assemblies and systems that provide a ball-and-socket or other articulation function in the body.

BRIEF SUMMARY OF THE INVENTION

In accordance with one aspect of the present invention, a prosthetic device may be generally a cup-shaped implant. In some examples, the cup shaped implant may be an acetabular cup. In one embodiment, the prosthetic device may have a cavity defined by an interior surface. The interior surface may include a partially spherical first portion and a partially cylindrical second portion. The relative position of each of the first and second portions is such that the second portion is recessed relative to the first portion. Both the first and second portions may extend from an interior edge of an end surface of the prosthetic device. When viewing the end surface in a direction orthogonal to a plane therethrough, a curve of the cylindrical second portion may be visible. Geometry of the interior surface of the device may allow an insert to be advanced in a single orientation over a particular portion of the cavity. When fully advanced into the prosthetic device, the insert may can be rotated such that it is constrained within the prosthetic device.

In accordance with another aspect of the present invention, a prosthetic assembly may be fabricated by placing an insert into a prosthetic device. The prosthetic device may be in the form of any shape with a cavity, which preferably may be defined by an interior surface of the device extending inward from an end surface of the prosthetic device. The cavity may be of sufficient size to accommodate advancement of an insert, that may be but is not limited to being a hollowed and partially spherical shape, from an end surface of the prosthetic device. Further, the cavity may be shaped by an interior edge of the end surface so that the insert may be inserted into the cavity in a corresponding manner and only in one alignment and orientation. The aligned and oriented insert may be advanced fully into the prosthetic device with its spherical center, which may be a spherical center when the insert is in the partially spherical shape, offset from a central plane through the prosthetic device. The insert is advanced until one part of a surface of the insert furthest from the opening of the cavity is proximal to the interior surface of the device. The prosthetic device may then be rotated within the device to bring it to a fully constrained position. Rotation of the insert from the fully advanced position is performed with little to no translation prior to rotation. In the constrained position, the insert may be constrained from falling out of or otherwise detaching from the device. Such constraint may be provided in particular by the interior surface of the prosthetic device near the end surface in which portions of the interior surface curve inwardly toward a center of the device, overlapping the insert to prevent it from exiting the cavity of the prosthetic device.

In another aspect of the present invention, a prosthetic device is provided that includes an exterior surface, an interior surface defining a cavity, and an end surface. The end surface includes exterior and interior edges and extends between the exterior and the interior surfaces. The interior edge of the end surface is defined at least in part by (i) a first curved portion having a first radius and (ii) a second curved portion having a second radius different from that of the first curved portion. A radial center of the first curved portion is offset from a radial center of the second curved portion such that a circumference defined by the first radius is entirely within a circumference defined by the second radius.

In one embodiment of the prosthetic device, the first curved portion defines the interior edge at two diametrically opposed locations. In another embodiment, the first curved portion contacts the second curved portion. In yet another embodiment, a prosthetic assembly includes the prosthetic device received in an acetabular cup and a cup-shaped implant.

In another aspect, the present invention relates to a prosthesis system. In one embodiment, the system includes a cup-shaped implant, a prosthetic device, an insert receivable in the prosthetic device and a prosthetic component having a stem attached to a ball joint receivable in the insert. The prosthetic device includes an exterior surface, an interior surface defining a cavity and an end surface. The end surface of the prosthetic device includes exterior and interior edges and extends between the exterior and the interior surfaces. The interior edge of the end surface is defined at least in part by (i) a first curved portion having a first radius and (ii) a second curved portion having a second radius different from that of the first curved portion. A radial center of the first curved portion is offset from a radial center of the second curved portion such that a circumference defined by the first radius is entirely within a circumference defined by the second radius. The prosthetic device is receivable in the cup-shaped implant.

In another embodiment, the insert is receivable in the prosthetic device in a first orientation relative to the prosthetic device and not receivable in the prosthetic device in a second orientation orthogonal to the first direction. In a variant of this embodiment, the first orientation aligns a curved surface of the insert with the second curved portion and the flat surface of the insert in a direction facing the first curved portion. In yet another embodiment, the second curved portion includes two second curved portions symmetrical about a plane through the prosthetic device, each of the two second curved portions having a geometry configured for advancement of a partially spherical structure therebetween.

In another aspect, the present invention relates to a prosthetic device that includes an exterior surface, an interior surface with first and second portions, and an end surface with exterior and interior edges and extending between the exterior and the interior surfaces. The second portion of the interior surface extends from the interior edge of the end surface at a right angle relative to the end surface and includes a step that abuts the first portion.

In one embodiment, the second portion of the interior surface has a depth extending from the interior edge of the end surface to a location at or below a maximum width of the interior surface measured in a plane parallel to the end surface. In another embodiment, the first portion of the interior surface extends from the interior edge of the end surface at an acute angle relative to the end surface at one or more locations of the first portion. In another embodiment, the end surface includes a width measured between the exterior and interior edges such that the width at one or more locations of the end surface abutting the second portion of the interior surface is narrower than the width abutting the first portion of the interior surface.

In yet another embodiment, the interior surface includes a third portion that shares an interior edge with the first portion and the second and the third portions include locations at maximum distances from a central axis of the first portion that is perpendicular to a plane defined by the end surface. The locations at maximum distances lie along a maximum separation axis offset from or at an angle to a first central plane through the interior surface. In a variant, the second and third portions of the interior surface are separated by the first portion. In another variant, the maximum separation axis is parallel to the first central plane. In yet another variant, the second and third portions of the interior surface are symmetrical about a second central plane through the interior surface normal to the first central plane. In still yet another variant, the second and third portions include indentations such that a partially spherical insert having a substantially flat end surface on a side thereof is insertable into the device only when the substantially flat end surface is positioned between the second and the third portions of the interior surface.

In another aspect, the present invention relates to a method of assembling a prosthetic assembly. In one embodiment, the method comprises steps of advancing an insert into a shell and rotating the advanced insert. In the advancing step, the insert is advanced into the shell with the insert oriented such that (i) a plane through a flat surface of the insert is transverse to a plane through an end surface of the shell, (ii) the flat surface is aligned with an indentation of an interior surface of the shell such that the plane through the flat surface of the insert passes through the indentation, (iii) a curved surface of the insert is received by a corresponding curvature of the interior surface of the shell, and (iv) the flat surface of the insert is offset from a central plane through the shell. In the rotating step, the advanced insert is rotated such that the flat surface of the insert is oriented in a different orientation than the orientation of the insert during advancement to constrain the insert within the shell.

In some embodiments, the rotating step follows the advancing step without translation of the insert. In other embodiments, the advancement continues until prevented by the interior surface of the shell. In other embodiments, when the advanced insert first contacts the shell, a gap between an outer surface of the insert and the interior surface of the shell increases as the distance from the flat surface of the insert increases. In still further embodiments, the flat surface of the insert sits proud of an annular end surface of the shell sharing an edge with the interior surface of the shell after the rotation of the insert.

DETAILED DESCRIPTION

Figure 1:
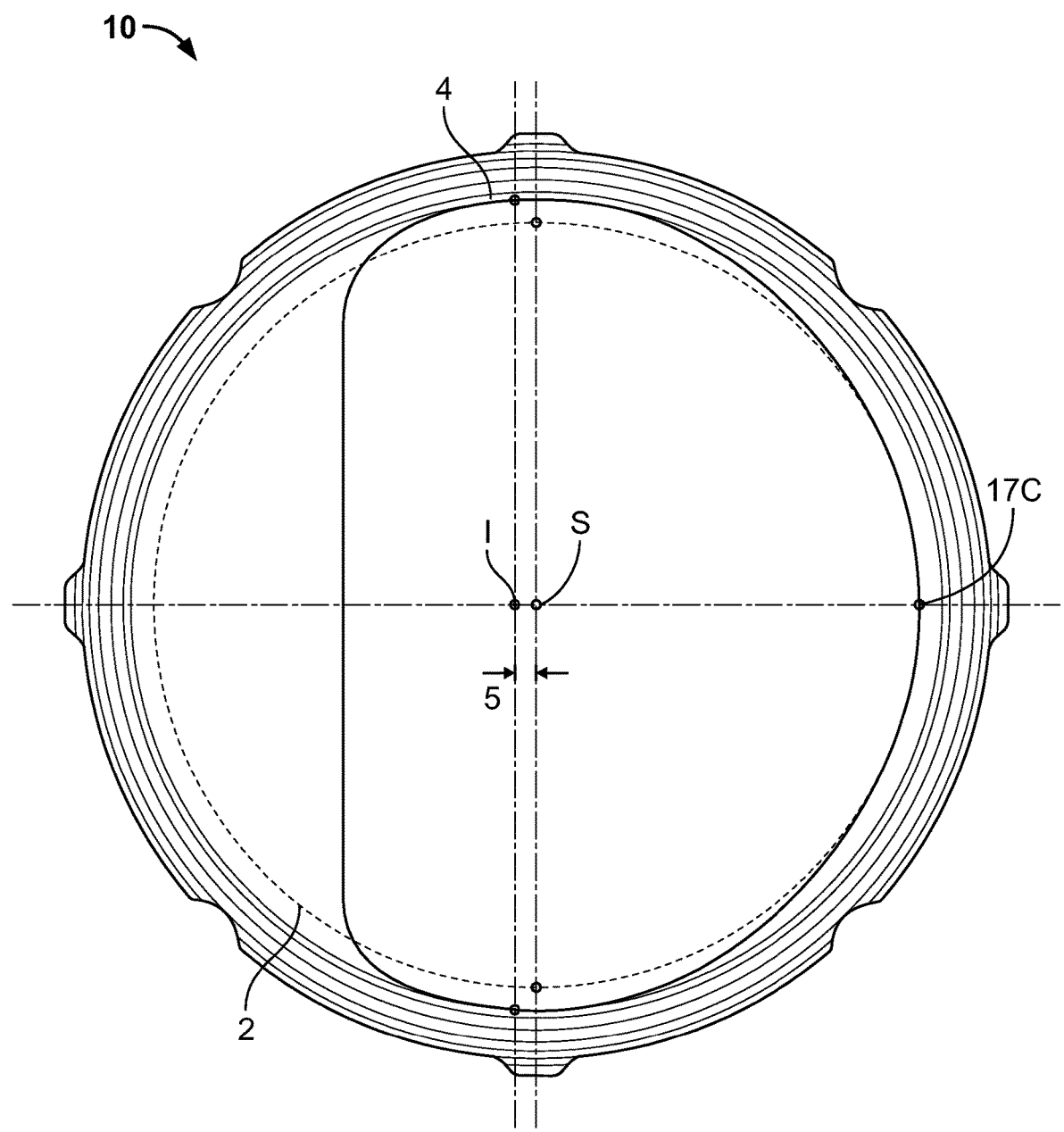
FIG. 1 is a top view of a shell along with dimensional lines demarcating curved surfaces and portions of the shell in accordance with an embodiment of the invention.

The present invention relates to improvements in the securement of elements in ball-and-socket joints, and in particular to multiple bearing joints such as modular dual mobility (MDM) joints. Although many embodiments described herein reference the hip joint, explanation of the invention in such context is non-limiting, and it is contemplated and to be understood that the invention can be used in other joints, such as but not limited to shoulder, elbow, wrist, and finger joints and in other contexts more generally.

Referring now to the drawings, as shown in FIGS. 1-5, shell 10 is a prosthetic device. More particularly, as shown, shell 10 is a liner which has an exterior surface 13 that, in some arrangements, may be used for placement into an acetabular cup and an interior surface described further herein for holding an insert, such as insert 20, for a femoral stem (FIG. 3A). As shown in FIG. 2A, shell 10 is symmetrical about plane 8. Plane 8 bisects shell 10 at a section as shown in FIG. 2B. As shown in FIGS. 2B and 2C, shell 10 includes a portion below a plane 9 and another portion above plane 9, the latter described herein as exterior surface rim depth 13A. The exterior and interior surfaces of the portion below plane 9 generally define a hemispherical shape. Exterior surface rim depth 13A of the portion above plane 9 extends from plane 9 in a generally cylindrical manner to annular end surface 16. The interior surface of the portion above plane 9 extending from plane 9 to annular end surface 16 is partially spherical and partially cylindrical, as seen in FIGS. 2B and 2C and described in greater detail below.

Figure 2A:
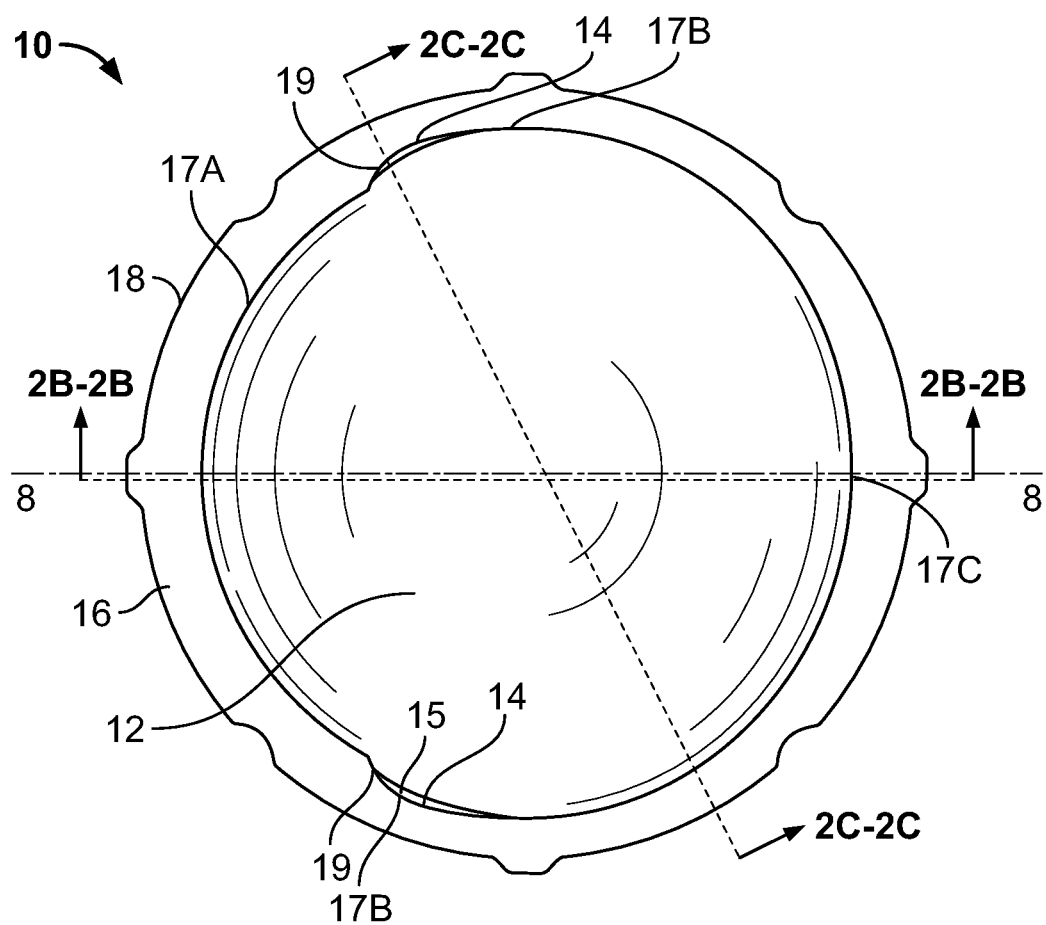
FIG. 2A is a top view of the shell of FIG. 1.
Figure 2B:
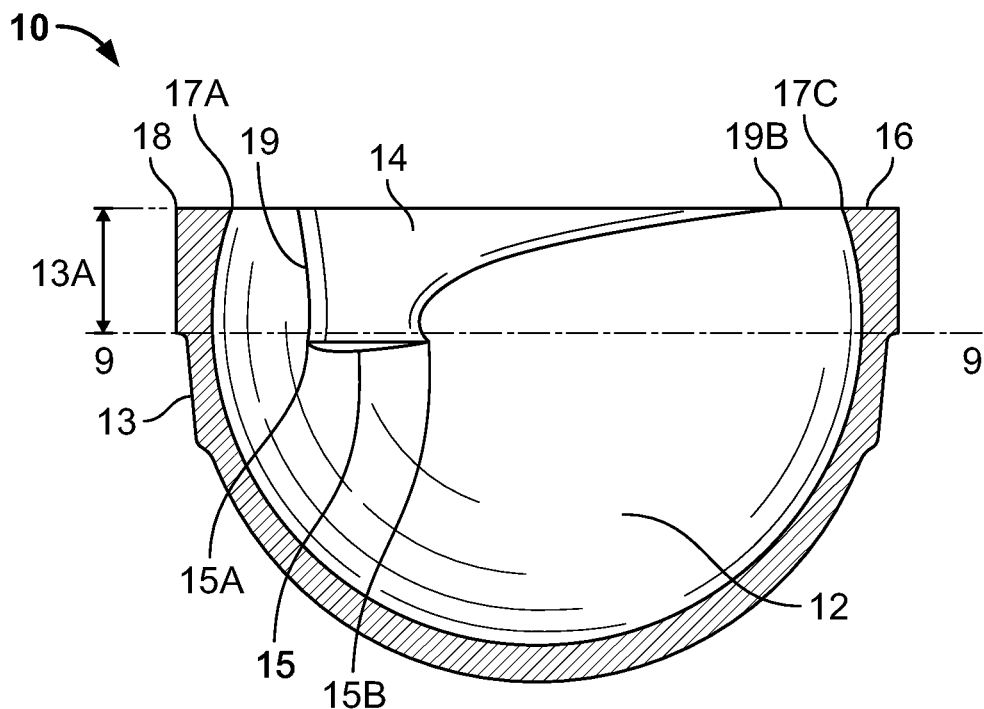
FIGS. 2B and 2C are cross-sectional views of the shell of FIG. 1 along the lines 2B-2B and 2C-2C shown in FIG. 2A.
Figure 2C:
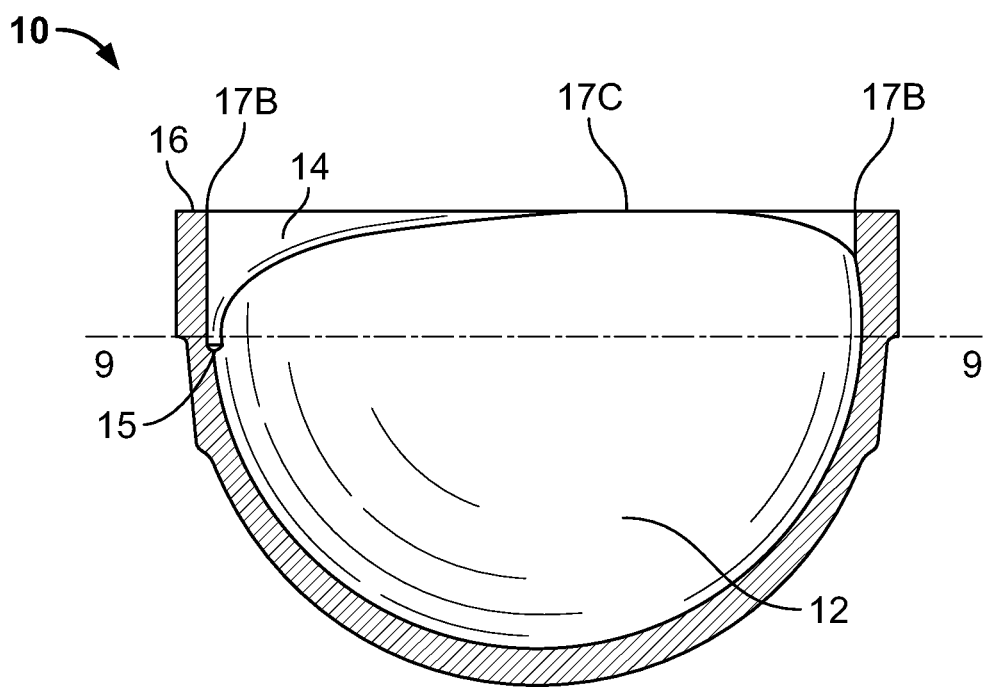

As best shown in FIGS. 2A-2C, the interior surface of shell 10 defines a cavity. The interior surface includes first portion 12 and symmetric second portions 14 extending from first portion 12 of the interior surface. Symmetric second portions 14 are symmetrical about plane 8 (FIG. 2A). The interior surface terminates at interior edges 17A, 17B, 17C of annular end surface 16. Annular end surface 16 extends around the perimeter of shell 10 and is bound by exterior edge 18 and interior edges 17A, 17B, 17C to define a thickness of shell 10.

Figure 2D:
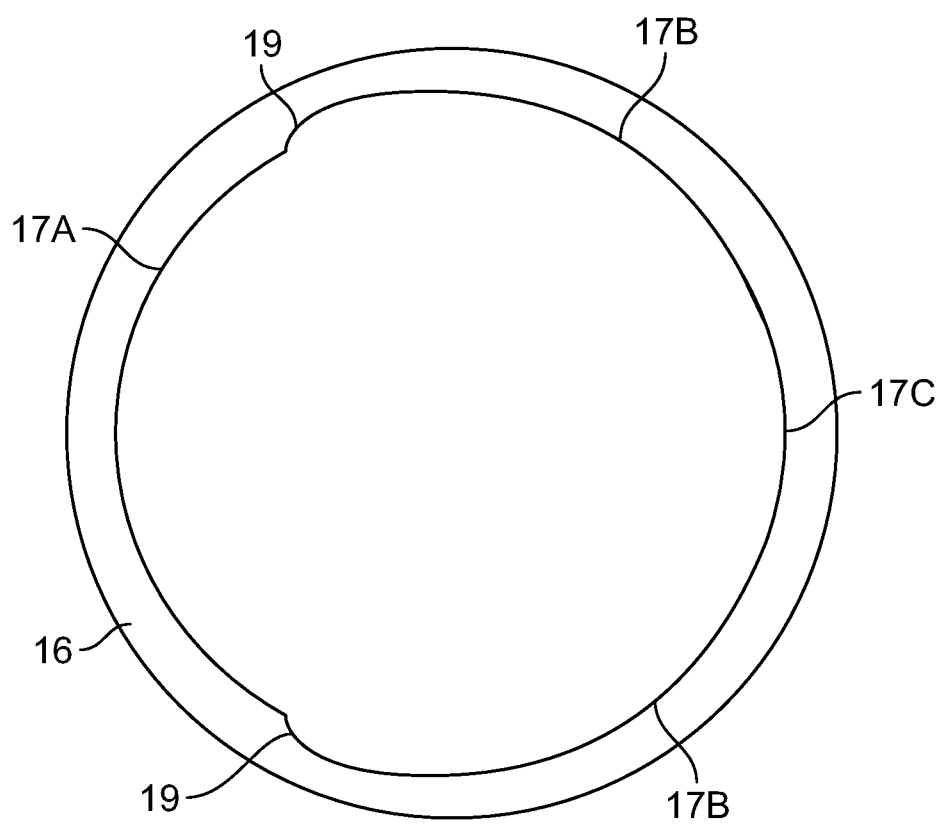
FIG. 2D is a top view of an annular rim of the shell of FIG. 1.

The shape of interior edges 17A, 17B, 17C is best described with reference to FIGS. 1, 2A and 2D. Interior edge 17A and interior edge point 17C (hereinafter also "interior edge 17C") define a portion of a circumference of circle 2 with a single radius centered at a location corresponding to a central axis S of shell 10. Symmetric interior edges 17B and interior edge point 17C define a portion of a circumference of circle 4, as shown in FIG. 1, with a single radius centered on a central axis I of a spherically shaped object, in this example insert 20, to be inserted into shell 10, described in greater detail below. The radii of respective edges 17A, 17B, 17C are such that the radius of circle 2 is smaller than that of circle 4. In the example shown, the radius for interior edge 17A is set at approximately 0.908 inches, and the radius for interior edges 17B is set at approximately 0.948 inches. In a preferred arrangement, the radius for interior edge 17A is set at approximately 0.895 to 0.935 inches, and the radius for symmetric interior edges 17B is set at approximately 0.948 inches. A relationship exists between an offset 5 of central axis I relative to central axis S and exterior surface rim depth 13A. For a given shell with interior edge 17B radius of 0.948 inches, corresponding axes, offsets and exterior surface rim depths are shown in Table 1 below:

TABLE 1

| Shell with a maximum interior edge radius of 0.948 inches | | | | | |
|---|---|---|---|---|---|
| Minimum interior edge radius (inches) | 0.935 | 0.928 | 0.919 | 0.908 | 0.895 |
| Offset of central axis I relative to central axis S (inches) | 0.013 | 0.020 | 0.029 | 0.040 | 0.053 |
| Exterior surface rim depth (inches) | 0.164 | 0.203 | 0.243 | 0.281 | 0.321 |

As demonstrated by Table 1, a shell with a larger or smaller maximum interior edge radius is contemplated that will also have increasing exterior surface rim depth corresponding to increasing offset between the central axes (i.e., I and S). The relationship between offset 5 and exterior surface rim depth 13A is scalable and not limited to a shell with a maximum interior edge radius of 0.948 inches as shown above. The values described in Table 1 may vary within a range limited at one extreme by a maximum amount of material removed from the interior surface of the shell and at the other extreme, by the minimum amount of material removed from symmetric second portions 14 relative to first portion 12 and proximal to junctures 19 necessary to create an interior edge with a perimeter sufficient in cross-sectional area for an insert to be advanced therein.

Further, and as shown in FIG. 1, central axis I is offset from central axis S so that the circumferences of the respective circles centered on central axes I and S are tangential at interior edge point 17C. In this way, circle 2 is entirely disposed within circle 4 except at interior edge 17C. As will be described in greater detail below, this geometry facilitates the advancement and constraint of an object within the cavity of shell 10.

First and symmetric second portions 12, 14 of the interior surface extend inward into the cavity of the shell directly from interior edges 17A, 17B, 17C, as shown in FIGS. 2A-2C. First portion 12 of the interior surface abuts interior edges 17A, 17C and extends inward from such edge at an acute angle, as best shown in FIG. 2B. First portion 12 of the interior surface is concave in shape in all directions, as best shown in the cross-sectional views of FIGS. 2B and 2C. In particular, the interior surface of first portion 12 forms a partial spherical shape slightly larger than an outer surface of a partially spherical insert to accommodate insertion of the insert into the cavity. Symmetric second portions 14 of the interior surface abut interior edges 17B, 17C. As seen in FIG. 2C in particular, a surface of each second portion 14 of the interior surface is perpendicular to a plane defined by annular end surface 16.

Junctures 19 are located at interfaces between interior edges 17B and interior edge 17A as seen in FIG. 2A, and have a length from annular edge surface 16 to a depth within the cavity of shell 10 that is below plane 9, corresponding to a first point 15A, as best shown in FIG. 2B.

The interior surface of shell 10 includes steps 15 at an interface between second portion 14 and first portion 12 and located at a maximum depth of second portion 14, at a furthest extent from annular end surface 16, as shown in FIGS. 2B and 2C. Steps 15 are symmetrical about plane 8, as shown in FIG. 2A. For ease of explanation, the geometry of one step is described below, but it is understood that the same geometry exists on the opposite side of shell 10. In some arrangements, step 15 may be formed by an indent into first portion 12. As in the example illustrated, step 15 may have a finite length parallel to end surface 16 extending from first point 15A to a second point 15B.

Returning to the geometry of symmetric second portions 14, from second point 15B toward the point at interior edge point 17C, the depth of second portion 14 lessens until terminating at interior edge point 17C, as best shown in FIGS. 2B and 2C. In this manner, a part of the interior edge at an end of symmetric second portions 14 opposite juncture 19 is abutted by the first portion (i.e., at interior edge 17C). Thus, each of symmetric second portions 14 of the interior surface are separated on all edges within the cavity by first portion 12. Described another way, symmetric interior edges 17B both extend to interior edge 17A at one end and interior edge point 17C at an opposite end. An approximate demarcation of each interior edge 17A, 17B, 17C is provided in FIG. 2D where points are included on the interior edge of annular end surface 16 to highlight the separation of each. The points identify the location of junctures 19 and interior edge point 17C for symmetric second portions 14 of the interior surface.

Continuing to refer to FIGS. 2B and 2C, first portion 12 of the interior surface of shell 10 forms an acute angle with annular end surface 16 at interior edges 17A, 17C, while symmetric second portions 14 of the interior surface form a right angle with annular end surface 16 at interior edges 17B. Described another way, the interior surface of shell 10 is partially spherical (first portion 12) with a partially cylindrical cutout (symmetric second portions 14) in which the center of the cylindrical cutout is offset from the center of the partially spherical surface. The depth of the cylindrical cutout is only partway into a depth of the interior surface, as seen in FIGS. 2A-2C.

In some arrangements, shell 10 is combined with a cup-shaped implant, such as an acetabular cup (not shown), to form an acetabular cup assembly. Exterior surface 13 of shell 10 is dimensioned to correspond to an interior surface of an acetabular cup sized for placement in the acetabulum of a patient. In some such arrangements, shell 10 rotates within the acetabular cup, providing a dual mobility (i.e., MDM) function when combined with additional elements as described in greater detail below.

Referring now to FIGS. 3A-5, the acetabular cup assembly described immediately above is combined with a prosthetic insert 20 into which a ball joint on a stem (not shown), such as but not limited to a ball joint of a femoral stem implant, may be inserted. Insert 20 is dimensioned for insertion into shell 10, and the stem is dimensioned to fit within a cavity defined by interior surface 22 of insert 20. Insert 20 includes a partially spherical external surface 28 and a flat end surface 26 which truncates the partially spherical surface. Interior surface 22 extends from flat end surface 26. In this manner, the stem extending from the ball joint may be articulated within the cavity defined by interior surface 22 when ball joint is inserted into insert 20.

Figure 3A:
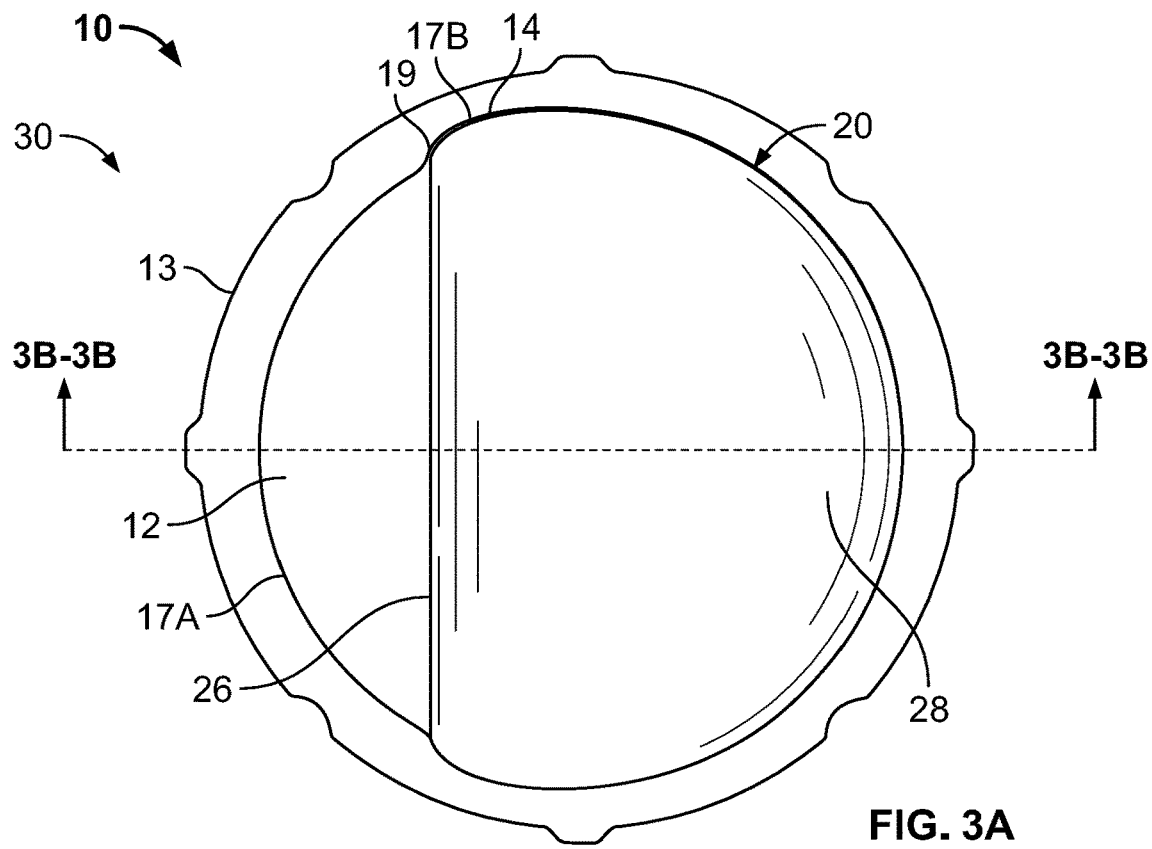
FIG. 3A illustrates a top view of an assembly of the shell of FIG. 1 and an insert disposed therein in accordance with an embodiment of the invention.

Insert 20 is dimensioned such that when aligned and oriented in a particular manner relative to shell 10, the insert can be advanced into the cavity of the shell through each of symmetric second portions 14 of the interior surface of shell 10. As shown in FIG. 3A, insert 20 must be positioned with a plane defined by flat end surface 26 normal to the plane defined by annular end surface 16 and with flat end surface 26 aligned with junctures 19 of symmetric second portions 14 for advancement into shell 10. In this position, a portion of flat end surface 26 between junctures 19 face first portion 12 of interior surface. The components as described, when combined, form a system which provides a dual mobility function. As such, shell 10 is rotatable and articulable within an acetabular cup, and, independently of shell 10, insert 20 is rotatable and articulable in shell 10 when inserted therein.

Material for shell 10 is any known to the ordinary artisan for socket elements used as part of a ball-and-socket joint. In the embodiments described herein, the insert is made of a polymer, which may be but is not limited to being ultra high molecular-weight polyethylene (UHMWPE), PEEK or polyurethane. In variants, the insert may be made of a ceramic, metal, such as but not limited to CoCr, or mixtures thereof, such as ceramicized metal. In further variants, other materials can be used as deemed suitable for desired applications.

Figure 3B:
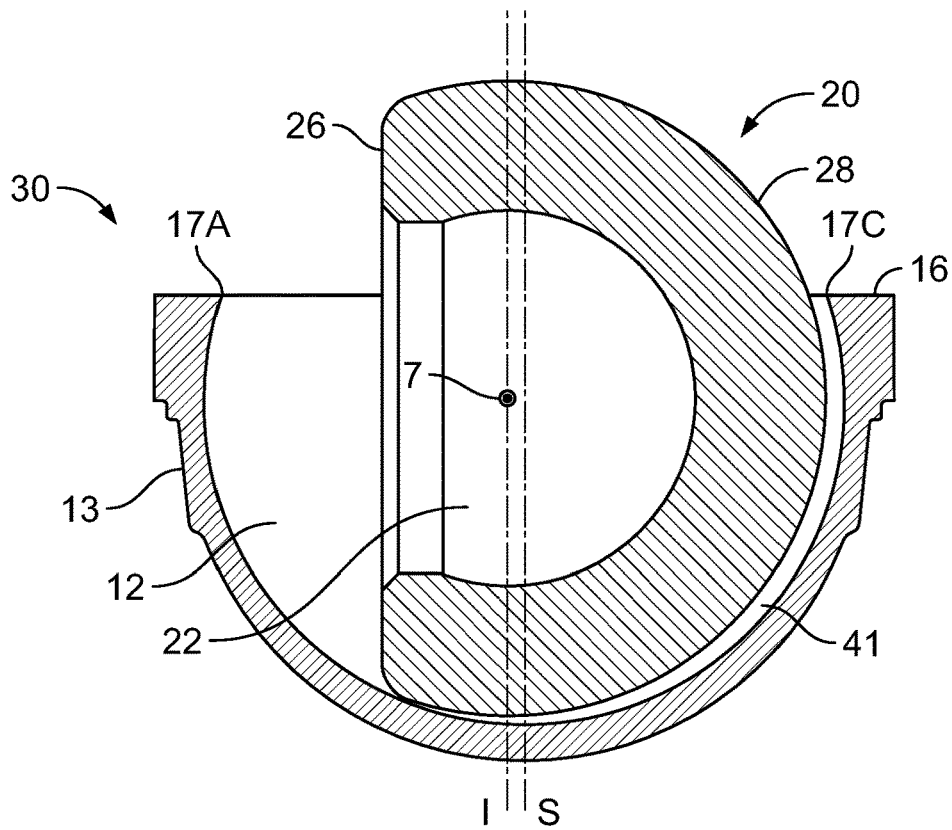
FIG. 3B illustrates an advancement step of the assembly of FIG. 3A along lines 3B-3B.

In accordance with another aspect of the invention, elements of assembly 30 are used in a method of fabrication. Referring to FIGS. 3A-5, in one example of fabricating assembly 30, insert 20 is provided external to shell 10. Insert 20 is then oriented such that its flat end surface 26 is perpendicular to annular end surface 16 of shell 10. In this manner, when flat end surface 26 of insert 20 is also positioned offset from center S of shell 10, as best shown in FIG. 3B, flat end surface 26 of insert 20 is aligned in a plane passing through both symmetrical second portions 14 of the interior surface. When aligned and oriented as described, insert 20 is advanced into the cavity of shell 10, as shown in FIGS. 3A and 3B. In this example, insert 20 is receivable in shell 10 in the orientation shown, but not in other orientations, such as an orientation orthogonal to that shown. During advancement, the orientation of insert 20 is maintained (see FIG. 3B). When external surface 28 of insert 20 contacts or is otherwise proximal to a bottom of first portion 12 of the interior surface at a maximum depth from annular end surface 16 of shell 10, as shown in FIG. 3B, advancement of insert 20 is complete. In this position, external surface 28 of insert 20 roughly corresponds to the interior surface of shell 10, but as seen in FIG. 3B, variable gap 41 is formed between the external surface of the insert and the interior surface of the shell when the insert is fully advanced. Gap 41 increases as the circumferential distance from flat end surface 26 of insert 20 increases.

Figure 4A:
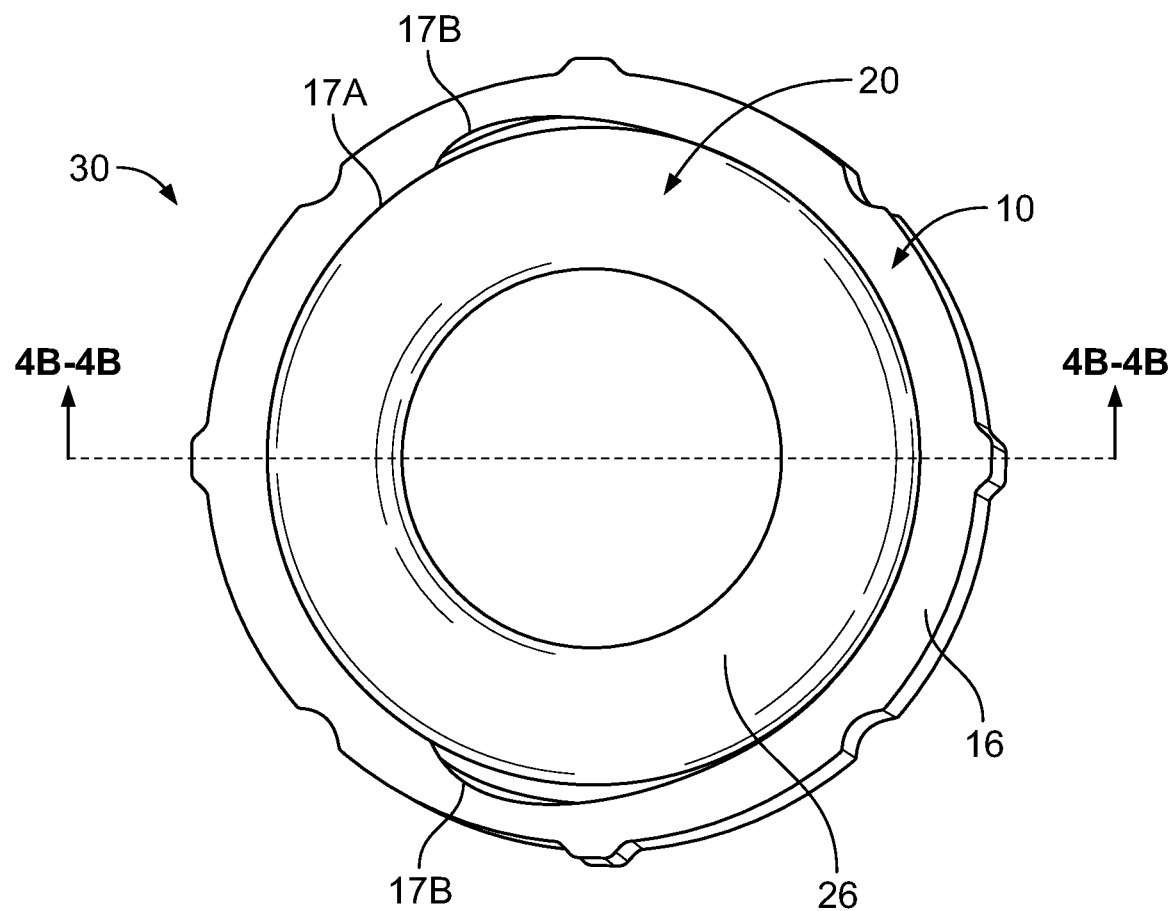
FIG. 4A is a top view of the assembly of FIG. 3A in which the insert is rotated to final insertion position.
Figure 4B:
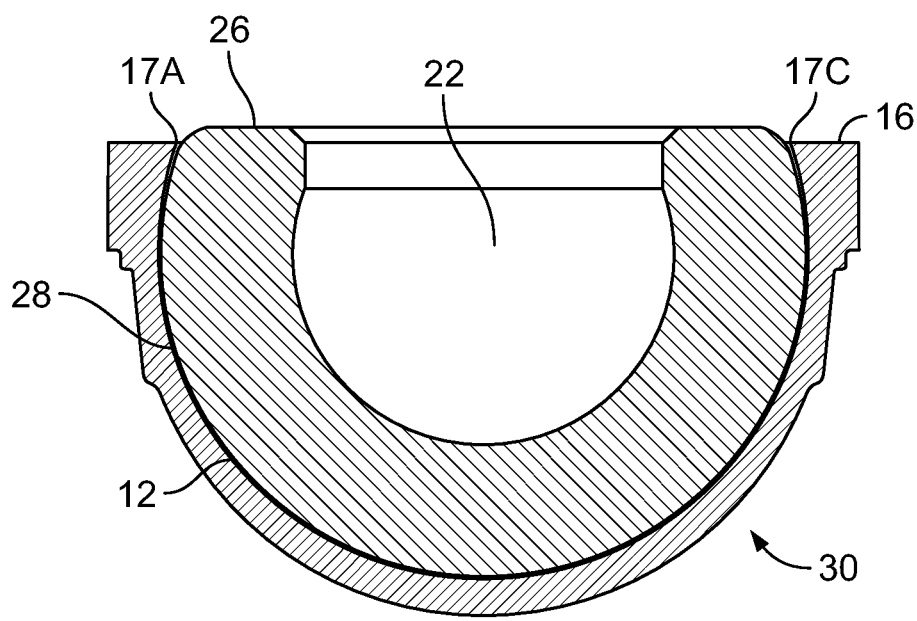
FIG. 4B is a cross-sectional view of the assembly of FIG. 3A along lines 4B-4B shown in FIG. 4A.
Figure 5:
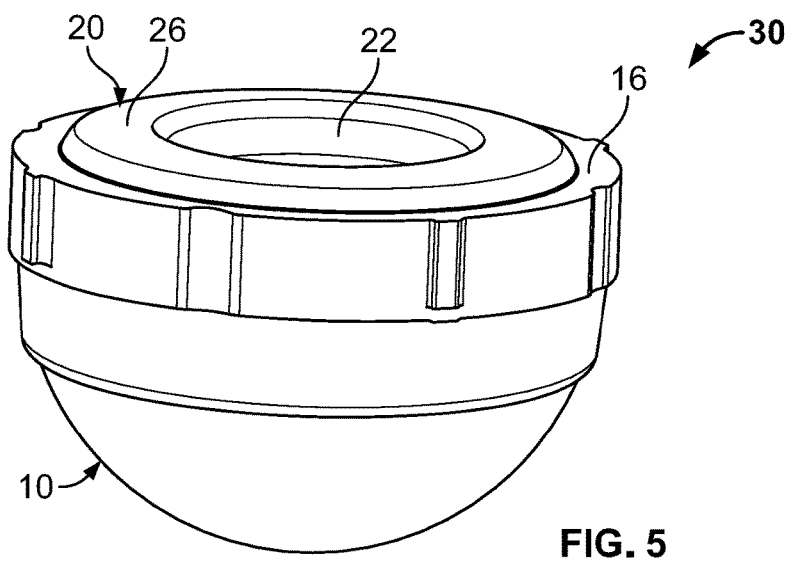
FIG. 5 is a perspective view of the assembly shown in FIG. 3A in the position shown in FIG. 4A.

Upon completion of advancement of insert 20, the insert is rotated such that a majority of external surface 28 corresponds to one of the first portion 12 or second portion 14 of the interior surface, as shown in FIG. 4B. In one example, insert 20 is rotated ninety degrees. Insert 20 is rotated following advancement with little or no translation and is rotated about an axis 7 (shown in FIG. 3B) through its center and parallel to flat end surface 26. If insert 20 was attempted to be rotated about another axis to rotate flat end surface 26, symmetric junctures 19 would impede and otherwise block any rotation from the fully inserted position shown in FIGS. 3A and 3B. When it is fully advanced and fully rotated, insert 20 sits proud of shell 10 as shown in FIGS. 4B and 5. Again with reference to FIG. 4B, when insert 20 is fully advanced and fully rotated in shell 10, insert 20 is constrained by the shell as first portion 12 of the interior surface proximal to interior edges 17A, 17C curves inwardly toward centers of shell 10 and over an edge at a maximum diameter of insert 20.

The close correspondence between surfaces of insert 20 and shell 10 provides additional protection against disengagement of insert 20. Because symmetric second portions 14 of the interior surface of shell 10 are lesser in depth closer to interior edge point 17C on one end of each of these portions and are separated from each other by first portion 12 on the other end of each of these portions, as shown in FIGS. 2B and 2C, inward facing interior surfaces of first portion 12 exist on opposite sides of a plane of shell 10 drawn between junctures 19 of symmetric second portions 14. In this manner, insert 20 is additionally constrained.

With insert 20 secured within shell 10, a ball joint on a stem (not shown) is inserted into the cavity of insert 20. In turn, the stem is then inserted into a bone, such as but not limited to a femur. The geometry of the shell and its interior surface optimizes the range of motion of an insert disposed therein. For example, because the fully advanced and fully rotated insert sits proud of the shell, the prosthetic stem disposed in the insert can be rotated over a wide range of angles compared to devices known in the art as the stem is not constrained by a surface of the shell extending above an end surface of the insert. The degree to which the stem can be rotated is a function of at least the diameter of the stem, the exterior surface rim depth of the shell and the width of the annular end surface of the shell. For example, if the exterior surface rim depth of the shell increases, the angle to which the stem may be rotated decreases. In this manner, the stem can be articulated, i.e., swiveled, up to approximately 180 degrees relative to a longitudinal axis through a center of the device opening (i.e., centerline S axis, as best shown in FIG. 3B), and preferably at least approximately 120 degrees.

The prosthetic device (e.g., shell), assembly, system and fabrication method may be varied in many respects. In some examples, a curved exterior (and/or interior) surface of the prosthetic device can be ellipsoidal or otherwise ovular in nature. In other examples, a cross-section of an end surface of the prosthetic device can be square, rectangular, or ovular, among other shapes. For any given prosthetic device, the end surface and curved surface may be any combination of these or other shapes. In at least some arrangements, part of an interior surface of the prosthetic device is defined by a second radius shaped to accommodate advancement of the insert and includes a center offset from a center of a first radius the prosthetic device. For example, where the external curved surface of the device is ellipsoidally shaped, the device may include a cavity with a corresponding ellipsoidal shape, separated from the external shape by an end surface.

The end surface in this example may be ellipsoidal or another shape. The interior surface may include a concave portion and another portion indented relative to the concave portion. The concave portion may have a radius smaller than that of the indented portion, and a center from which the radius of the concave portion is measured may be offset from a center of the radius for the indented portion.

Figure 6:
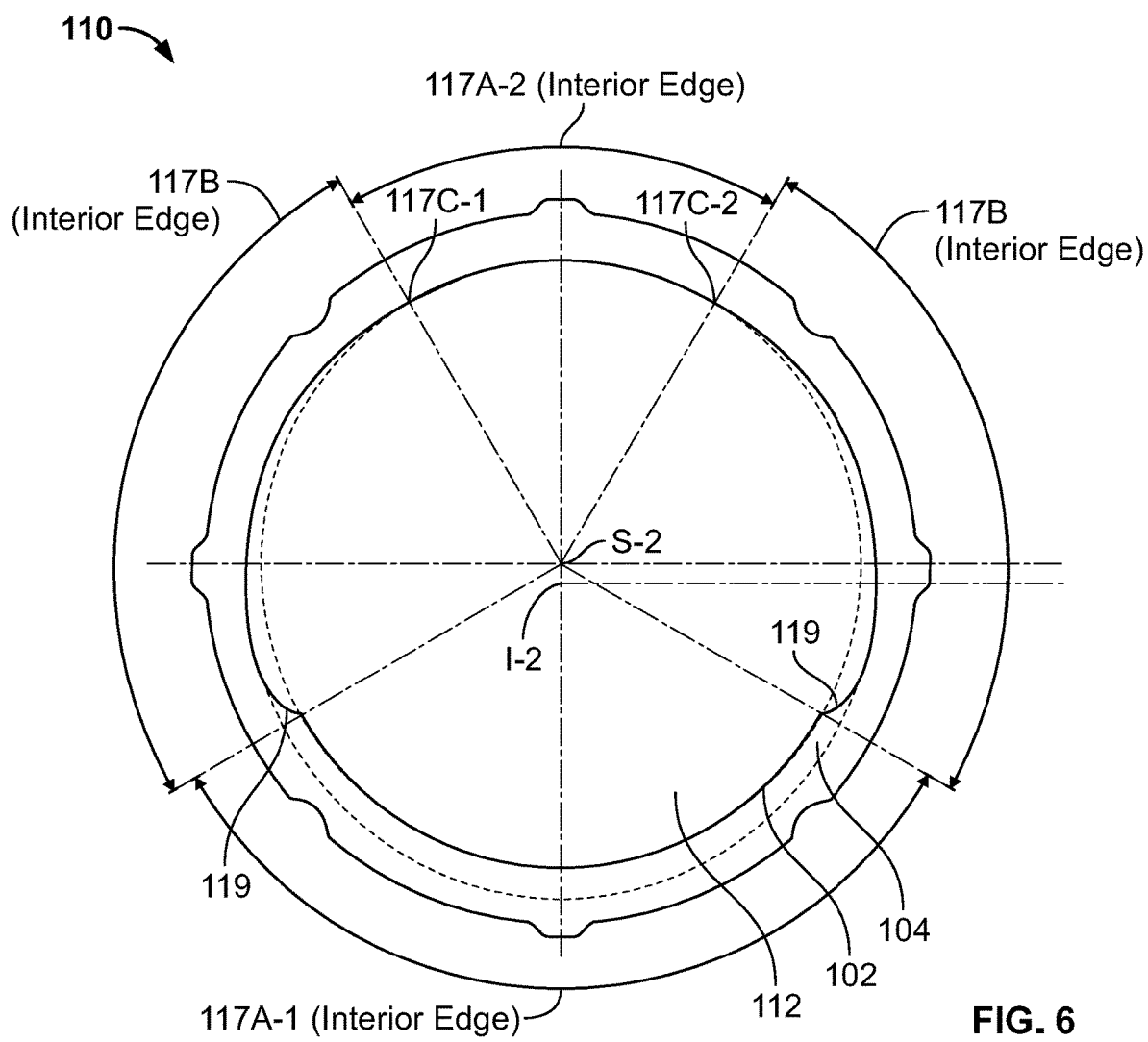
FIG. 6 is a top view of a shell in accordance with another embodiment of the invention.

As shown in FIG. 6, in another arrangement, a shell 110 includes interior edges 117A-1, 117A-2 defined by a portion of a circumference of a smaller circle 102, and interior edges 117B defined by a portion of a circumference of a larger circle 104. Smaller circle 102 overlaps with larger circle 104 at points 117C-1 and 117C-2. As with the embodiments described above, a center S-2 of circle 102 is offset from a center I-2 of circle 104. The overlap between circles 102, 104 creates an interior edge with four portions: two opposing portions defined by the circumference of smaller circle 102 (i.e., interior edges 117A-1, 117A-2), and two opposing portions defined by the circumference of larger circle 104 (i.e., interior edges 117B), such portions dividing interior edges 117A-1, 117A-2. Interior edge 117A-1 extends between opposing junctures 119 while interior edge 117A-2 extends between points 117C-1 and 117C-2 such that interior edge 117B extends between one of junctures 119 and one of points 117C-1 and 117C-2. An interior surface of shell 110 includes a first portion 112 and a second portion (not shown) as described in the embodiments described previously herein.

In some examples, the prosthetic device may be configured to function both as an acetabular cup and a liner for an insert, thus removing the need for an additional element between the prosthetic device and the acetabulum when implanted in a patient. In another example, the cup-shaped implant, e.g., acetabular cup, may include a locking mechanism, such as but not limited to a morse taper, that corresponds to a feature on the prosthetic device such that when combined, the cup-shaped implant and the prosthetic device are fixed and do not rotate relative to one another. In other examples, the insert may be a femoral head monolithic with, and thus inseparable from, a stem. In other embodiments, the prosthetic device may be configured and shaped for use in locations of the body other than the hip, for example, in the shoulder, elbow, wrist or finger.

Figure 7:
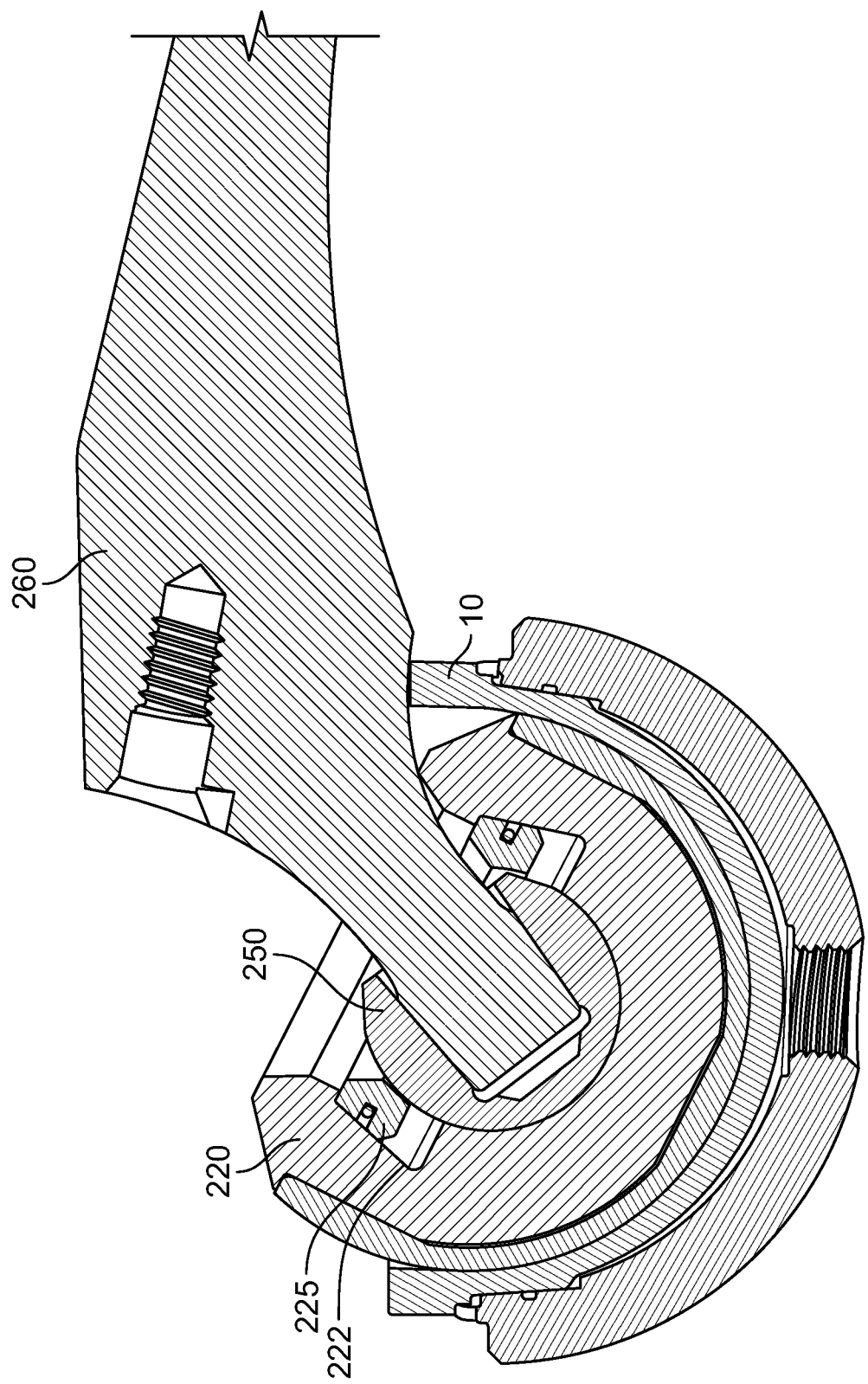
FIG. 7 is a cross-sectional view of an assembly having the shell of FIG. 1 and a femoral implant disposed therein in accordance with another embodiment of the invention.

As shown in FIG. 7, in some embodiments, retaining ring 225, which as in the example shown may be a plastic slotted ring surrounded by an internal wire, is positioned along inner groove 222 of insert 220. Retaining ring 225 slides inward and away from an opening of insert 220 as femoral head 250 is advanced into insert 220 and against the retaining ring, expanding the retaining ring and minimizing the force necessary for advancement of the insert. When femoral head 250 is fully advanced into insert 220 with a maximum diameter of the femoral head past retaining ring 225, the retaining ring contracts to a smaller diameter and returns toward its initial position proximate the opening of insert 220, as shown in FIG. 7. In this manner, retaining ring 225 secures femoral head 250 in position within insert 220 and thus allows the femoral head to be advanced into the insert by hand without resistance from the insert and thus without any tools. In employing this assembly, insert 220 can be inserted into shell 10 first, then rotated into a secure position, in a manner similar to that shown for insert 20 in FIGS. 3B and 4B, and then femoral head 250 and stem 260 inserted into and extending from the head can be inserted separately thereafter. An applicable variant of such assembly of a femoral head to an insert using a locking ring is described in *Trident Constrained Acetabular Insert: Surgical Protocol*, by Stryker, copyright 2012, hereby incorporated by reference herein in its entirety. In other embodiments, the interior surface of the insert does not include a retaining ring. Examples of such a configuration are shown in FIG. 3B and in *MDM X3: Surgical Technique* by Stryker, copyright 2012, hereby incorporated by reference herein in its entirety.

In still further arrangements, the interior surface of the shell may include a single second portion indented relative to a first portion such that an entire interior surface of the shell includes only one first portion and only one second portion. In these arrangements, the second portion may include geometric features as described above. Of course, the features described in the various examples and embodiments herein are contemplated as being configured for use in combination with one another. In addition, it is contemplated that the methods of the present invention may be employed using the various alternative embodiments described.

In some arrangements, after fabricating a prosthetic assembly such as assembly 30, the combined insert and shell may be advanced into a cup-shaped implant, such as an acetabular cup. Alternatively, the shell may be advanced into the acetabular cup prior to advancement of the insert into the shell. In any of the above embodiments, a prosthetic stem may be inserted into the insert. At any point prior to assembly with the shell, the acetabular cup may be inserted into an acetabulum of a patient. Where the shell is disposed in an acetabular cup, the combined system provides dual mobility functionality, as described above.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A partially spherical prosthetic device comprising:
an exterior surface;
an interior surface defining a cavity; and
an end surface extending between the exterior and the interior surfaces,
wherein the end surface adjoins the interior surface along a closed perimeter to form an interior edge, the interior edge being defined at least in part by (i) a first curved edge portion having a first radius and (ii) a second curved edge portion having a first edge part having a second radius different from that of the first curved edge portion,
wherein the end surface meets the interior surface at an acute angle over an entirety of a first length of the first curved edge portion and the end surface meets the interior surface at a right angle over an entirety of a second length of the second curved edge portion,
wherein a radial center of the first curved edge portion is offset from a radial center of the first edge part of the second curved edge portion such that a first circumference defined by the first radius is partially within a second circumference defined by the second radius and the first and the second circumference share a tangent line, and
wherein the first curved edge portion and the second curved edge portion define an entirety of the closed perimeter of the device.

2. The partially spherical prosthetic device of claim 1, wherein the first curved edge portion defines the interior edge at two diametrically opposed locations.

3. The partially spherical prosthetic device of claim 1, wherein the first curved edge portion contacts the second curved edge portion.

4. The partially spherical prosthetic device of claim 1, wherein the second curved edge portion includes two second curved edge portions symmetrical about a plane through the partially spherical prosthetic device, each of the two second curved edge portions having a geometry configured for advancement of a partially spherical structure therebetween.

5. The partially spherical prosthetic device of claim 1, wherein the second length of the second curved edge portion is longer than the first length of the first curved edge portion.

6. A prosthetic assembly comprising:
a cup-shaped implant; and
the partially spherical prosthetic device of claim 1 received in the cup-shaped implant.

7. A prosthetic device comprising:
an exterior surface;
an interior surface having a first surface portion and a second surface portion; and
an end surface extending between the exterior and the interior surfaces,
wherein the end surface adjoins the interior surface along a closed perimeter to form an interior edge,
wherein the end surface meets the first surface portion of the interior surface at an acute angle, the end surface adjoining the first surface portion over a first length of the interior edge wherein the acute angle extends over an entirety of the first length,
wherein the end surface meets the second surface portion of the interior surface a right angle, the end surface adjoining the second surface portion over a second length of the interior edge, wherein the right angle extends over an entirety of the second length,
wherein the first length of the interior edge and the second length of the interior edge define an entirety of the closed perimeter of the device, and
wherein the interior surface includes a step between the first surface portion and the second surface portion, the step being spaced apart from the end surface.

8. The partially spherical prosthetic device of claim 7, wherein the second surface portion of the interior surface has a depth extending from the interior edge to a location at or below a maximum width of the interior surface measured in a plane parallel to the end surface.

9. The partially spherical prosthetic device of claim 7, wherein the end surface includes a width measured between interior edge and an exterior edge formed by the intersection of the exterior surface and the end surface, wherein the width at one or more locations of the end surface abutting the second surface portion of the interior surface is narrower than the width at one or more locations of the end surface abutting the first surface portion of the interior surface.

10. The partially spherical prosthetic device of claim 7, wherein the second surface portion includes a first subportion and a second subportion, and
wherein the first subportion and the second subportion include locations at maximum distances from a central axis of the first surface portion that is perpendicular to a plane defined by the end surface, wherein the locations at maximum distances lie along a maximum separation axis offset from or at an angle to a first central plane through the interior surface.

11. The partially spherical prosthetic device of claim 10, wherein the first subportion and second subportion include indentations such that a partially spherical insert having a substantially flat end surface on a side thereof is insertable into the partially spherical prosthetic device only when the substantially flat end surface is positioned between the first subportion and the second subportion of the interior surface.

12. The partially spherical prosthetic device of claim 10, wherein ends of each of the first subportion and the second subportion of the interior surface are separated by the first surface portion.

13. The partially spherical prosthetic device of claim 10, wherein the maximum separation axis is parallel to the first central plane.

14. The partially spherical prosthetic device of claim 13, wherein the first subportion and the second subportion of the interior surface are symmetrical about a second central plane through the interior surface normal to the first central plane.

15. The partially spherical prosthetic device of claim 7, wherein the step has a first edge abutting the first surface portion and a second edge abutting the second surface portion.

16. The partially spherical prosthetic device of claim 15, wherein at least part of the second edge is located at a maximum depth of the second surface portion from the end surface.

17. A system comprising:
the partially spherical prosthetic device of claim 1; and
an insert receivable in the partially spherical prosthetic device.

18. The system of claim 17, wherein the insert is receivable in the partially spherical prosthetic device in a first orientation relative to the partially spherical prosthetic device and not receivable in the partially spherical prosthetic device in a second orientation orthogonal to the first orientation.

19. A system comprising:
the partially spherical prosthetic device of claim 7; and
an insert receivable in the partially spherical prosthetic device.

20. A partially spherical prosthetic device comprising:
an exterior surface;
an interior surface having a first surface portion and a second surface portions; and
an end surface having exterior and interior edges and extending between the exterior and the interior surfaces,
wherein the end surface adjoins the interior surface along an inner perimeter to form the interior edge,
wherein the end surface meets the first surface portion of the interior surface at an acute angle such that the first surface portion extends from a first curved edge portion of the interior edge at an acute angle relative to the end surface over an entirety of a first length of the first curved edge portion of the interior edge,
wherein the end surface meets the second surface portion of the interior surface at a right angle such that the second surface portion extends from a second curved edge portion of the interior edge at a right angle relative to the end surface over an entirety of a second length of the second curved edge portion of the interior edge, and
wherein the first curved edge portion and the second curved edge portion define an entirety of an inner perimeter of the device and the second curved edge portion lacks an interruption over its length along the inner perimeter.

* * * * *